United States Patent [19]
Morris

[11] Patent Number: 5,947,957
[45] Date of Patent: Sep. 7, 1999

[54] PORTABLE LASER FOR BLOOD SAMPLING

[75] Inventor: James H. Morris, Encinitas, Calif.

[73] Assignee: JMAR Technology Co., San Diego, Calif.

[21] Appl. No.: 08/529,506

[22] Filed: Sep. 18, 1995

Related U.S. Application Data

[63] Continuation-in-part of application No. 08/363,751, Dec. 23, 1994.
[51] Int. Cl.$^6$ ...................................................... A61N 5/06
[52] U.S. Cl. ..................................... 606/13; 606/2; 606/9; 606/10; 600/573; 600/576; 600/578
[58] Field of Search .................. 606/2–19; 600/573–578

[56] References Cited

U.S. PATENT DOCUMENTS

| | | | |
|---|---|---|---|
| 3,547,125 | 12/1970 | Tagnon | 606/4 |
| 5,165,418 | 11/1992 | Tankovich | 606/16 |

*Primary Examiner*—David M. Shay
*Attorney, Agent, or Firm*—Baker & McKenzie

[57] ABSTRACT

A portable laser device for obtaining blood samples through the skin of humans or animals. A laser crystal is optically pumped to produce a short high power laser pulse which vaporizes a small hole in the skin. The pulse is shaped to produce a pulse cross section at a sampling location which has a long dimension and a short dimension similar to a blade cut.

14 Claims, 7 Drawing Sheets

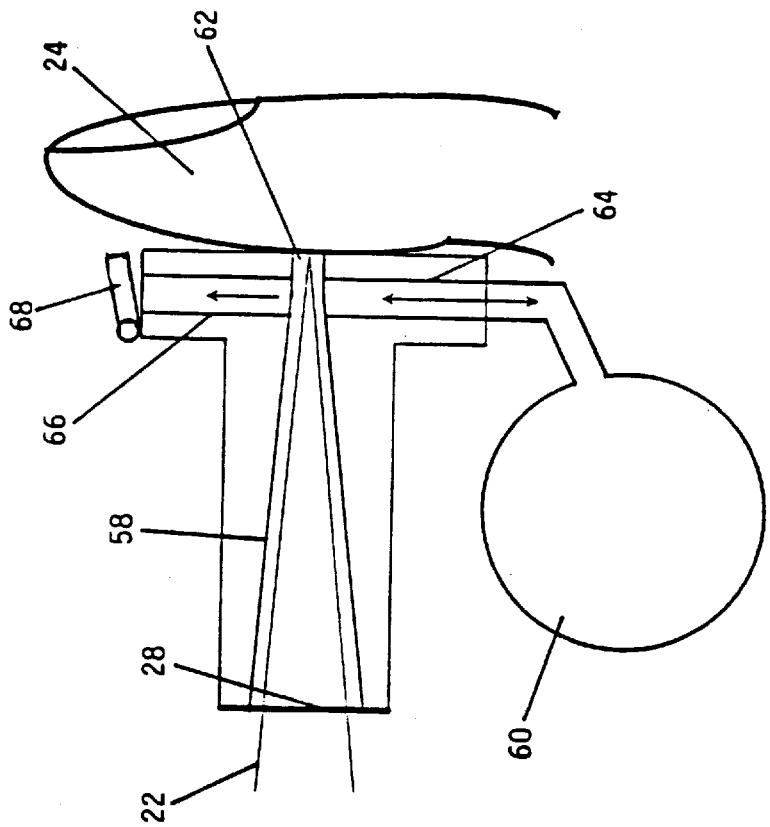
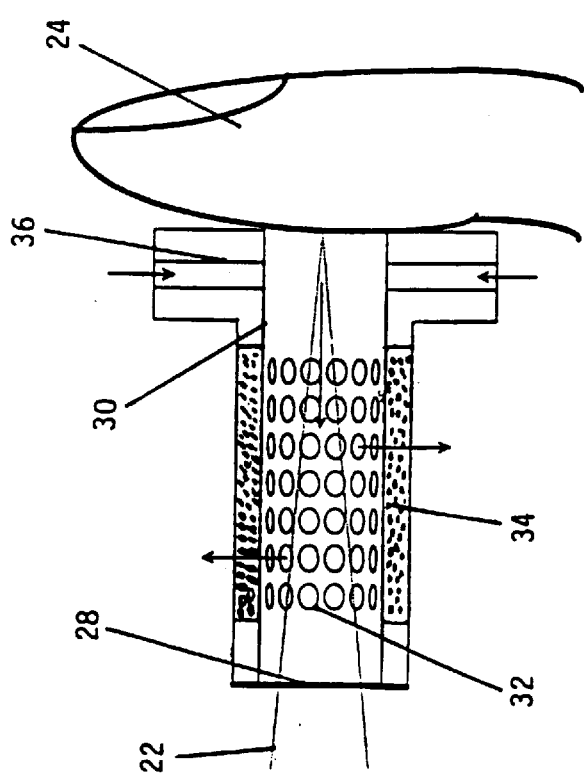
FIG. 3B
FIG. 3A

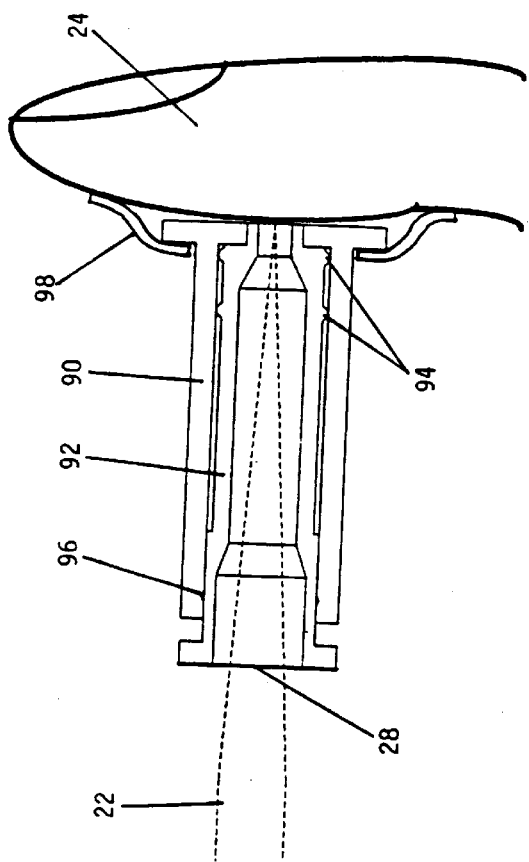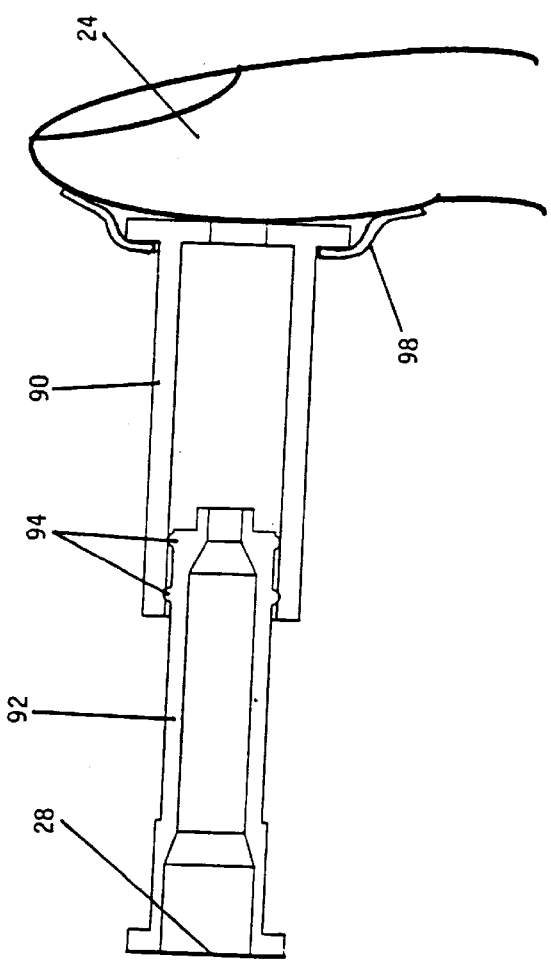

PORTABLE LASER FOR BLOOD SAMPLING

This application is a continuation in part of Ser. No. 08/363,751 filed Dec. 23 1994. This invention relates to lasers devices and in particular to laser devices for obtaining blood samples.

BACKGROUND OF THE INVENTION

The taking of blood samples is a very important part of the process of diagnosing and controlling disease. The traditional method used for taking small blood samples for blood formula and glucose measurement is to puncture the skin of a finger with a sharp object like a needle or pointed blade. For the taking of larger samples for other blood analysis a vein is usually punctured with a syringe needle. These methods are almost always painful and often frightening to many people, especially children. In addition there is a growing concern regarding the possibility of contracting AIDS by contaminated needles and blades. The use of animals in medical research is very common, especially small animals such as mice and rats. Many blood samples from these animals are needed. The common method of obtaining blood samples from mice and rats is to chop off a rearward most section of the animals tail.

On Nov. 24, 1992 a patent disclosing a blood sampling device and method using a laser, (U.S. Pat. No. 5,165,418) was issued to Dr. Nikolai I. Tankovich. The method described in that patent involved use of a short pulse Erbium laser to vaporize a hole in the skin of sufficient size to obtain the desired blood sample. Methods and devices were described to obtain small samples of one or two drops and larger samples of several grams.

Erbium lasers have been available commercially for several years. The wavelength of the laser produced by the Erbium laser is 2.94 microns. This wavelength is very absorptive in human and animal tissue, thus, the energy of the beam is absorbed in and vaporized skin tissue as explained in the Tankovich patent.

Commercially available Erbium lasers are not well adapted for use in blood sampling. Most are much too expensive. The typical disposable blade costs about 6 cents. The cost of Erbium lasers is currently in the range of several thousand dollars each. There is a concern regarding vapors produced during the sampling process, especially when there is a real or suspected possibility of AIDS contamination. Most of the current Erbium lasers are not easily portable by medical personnel.

A better method of obtaining blood samples from humans and animals is needed.

SUMMARY OF THE INVENTION

The present invention provides a portable laser device for obtaining blood samples through the skin of humans or animals. A laser crystal is optically pumped to produce a short high power laser pulse which vaporizes a small hole in the skin. The pulse is shaped to produce a pulse cross section at a sampling location which has a long dimension and a short dimension similar to a blade cut.

BRIEF DESCRIPTION OF THE DRAWINGS

FIGS. 3A, B, C and D show views of disposable tips.

DETAILED DESCRIPTION OF PREFERRED EMBODIMENTS

A preferred embodiment of the present invention can be described by reference to the drawings.

First Preferred Embodiment

Figure 1:
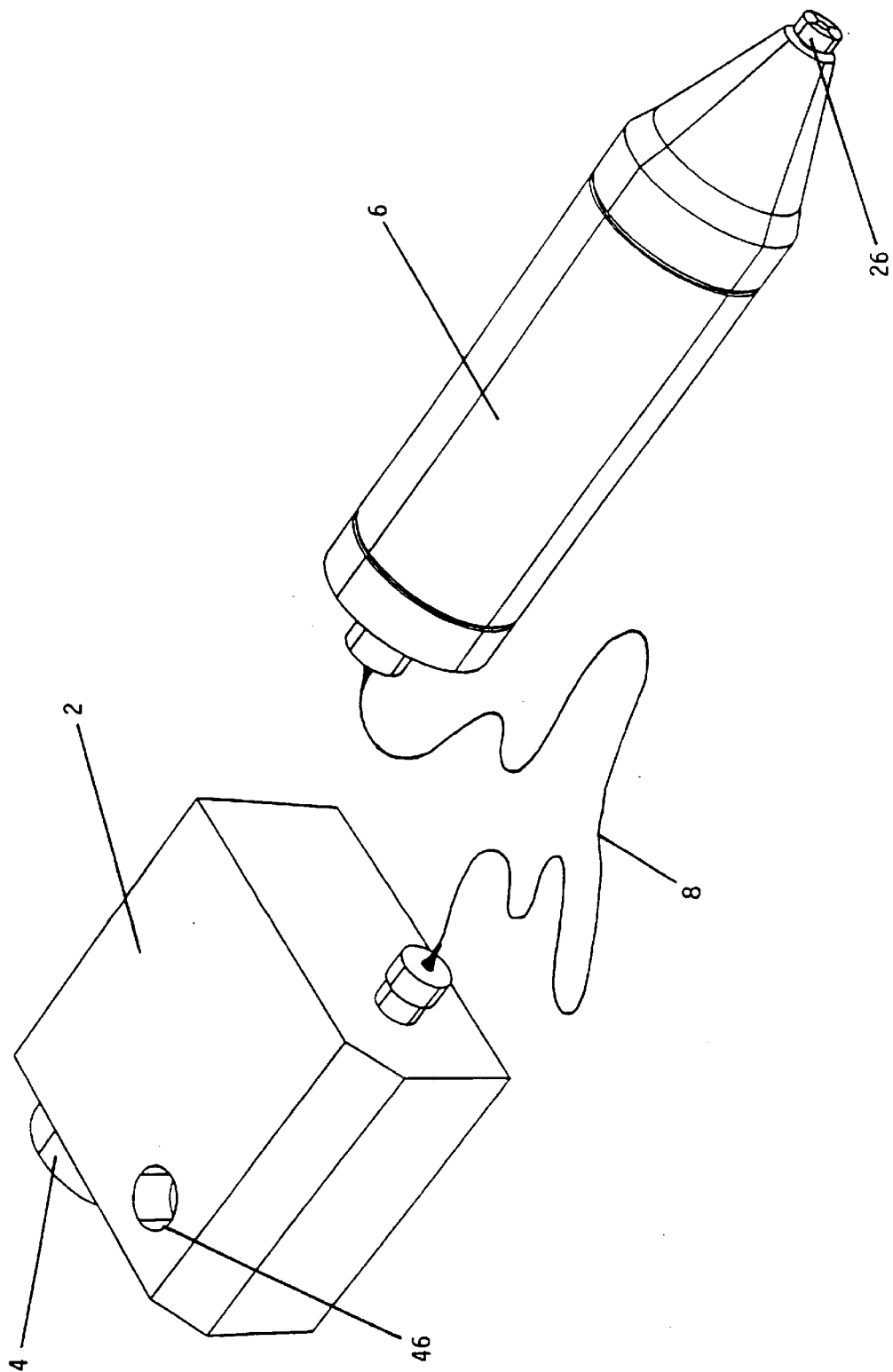
FIG. 1 is a drawing of a preferred embodiment of the present invention.

As shown in FIG. 1, this embodiment includes portable power base unit 2, power module 4 which is a part of but is removable from the base unit 2 and hand held laser unit 6 and disposable tip unit 26 which is a part of but removable from laser unit 6. Laser unit 6 is connected to power base unit 2 by flexible power cord 8. A calibration port 46 is provided in base unit 2.

Hand Held Laser Unit

Figure 2:
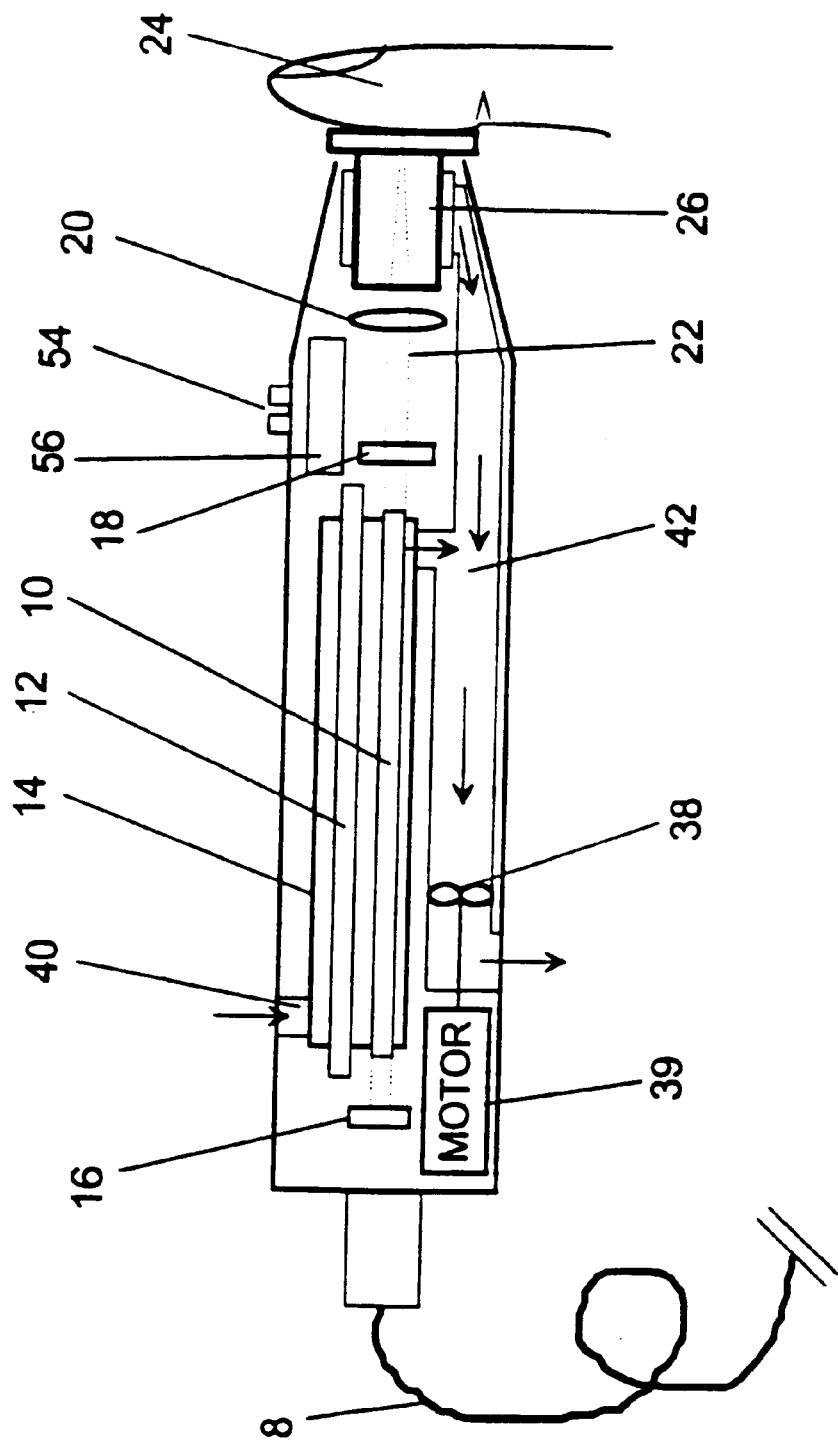
FIG. 2 shows details of the above embodiment.

Hand held laser unit 6 as shown in FIG. 2 comprises a 3 mm diameter by 75 mm long Erbium-YAG crystal 10 (as available from sources such as Scientific Materials, Corp.), a 3 mm by 63 mm arc cerium doped quartz xenon flashlamp 12 (as available from sources such as ILC Technology, Inc.) contained in pump cavity 14 which is provided with reflective interior walls. The optical resonator is comprised of a maximum reflector 16 and a 15 percent output coupler 18 (both available from suppliers such as Lightning Optical Co). The output of the laser is focused by IR transmitting quartz lens 20 which has a focal length of 25 mm. This lens focuses the beam 22 to a spot size of 0.025 mm$^2$ at the extremity of the laser unit onto the surface of the skin of the finger 24 of a patient. In a preferred mode of operation a single pulse of 0.15 joules (6 joules per mm$^2$) vaporizes a hole of about 0.025 mm$^2$ in cross section and 0.5 mm deep in the skin of the finger. Switches and indicator lights 54, located on the barrel of the hand held unit, control operation of the system. Trigger transformer 56 within the hand held unit converts a low voltage trigger pulse from the base unit 2 to a low energy 10 kV voltage spike to initiate the flashlamp discharge.

Flow-Through Disposable Tip Unit

To avoid any possible transmission of blood contamination from one patient to another, laser unit 6 comprises a flow-through disposable tip unit 26. A drawing of a flow through disposable tip unit 26 is shown in FIG. 3A. Tip unit 26 comprises a plastic film 28 (such as polyethylene) that is transparent to the laser beam 22 and is sealed to the end of the walls of cylinder 30. The central portion of cylinder 30 contains tiny holes 32 and the outside of cylinder 30 is lined with activated charcoal and filter paper 34. The bottom portion of tip unit 26 is flared to a diameter of 1 cm and small holes as shown at 36 permit air to be drawn in through tip unit 26 and through charcoal liner 34 by fan unit 38 as shown in FIG. 2. Thus, skin tissue vaporized during the sampling is effectively vacuumed into the charcoal liner. In this embodiment fan unit 38, driven by motor unit 39, also provides cooling for the laser pump cavity by causing air to flow from port shown at 40 through the cavity. The air exits as shown at 42. With this cooling a duty factor of up to 10 pulses per minute is possible. Duty factors in this range is preferred because several pulses may be required for some people with very thick skin.

Sealed Disposable Tip Unit

An alternative sealed tip unit 26 is shown in FIG. 3B. Side walls 58 are solid and tapered to minimize volume. Laser beam 22 passes through transparent plastic film 28 that is sealed to the end of wall 58. After finger 24 seals aperture 62, bulb 60 is compressed forcing air through holes 64 and 66 into the atmosphere. Check valve 68 seals hole 66 maintaining a partial vacuum within the tip. After the laser fires finger 24 is removed and air entering aperture 62 and vaporized tissue captured in the tip are sucked into the bulb 6. Bulb 60 and tip unit 26 are disposable. A third alternate tip 26 shown in FIG. 3C provides both vapor trapping and blood collection capabilities. The unit is comprised of a blood collection cylinder 90 and a vapor collection cylinder 92. A plastic film 28, transparent to the laser beam, seals the end of the vapor cylinder 92. Cylinder 92 is similar to the plunger of a syringe, it can be moved relative to cylinder 90 and yet maintain a seal provided by soft collars 94. The unit is taped onto finger 24 with adhesive tape 96. The tip unit is inserted into hand held laser unit 6 and the laser pulse 22 vaporizes a tiny hole in finger 24. Vaporized tissue and solid debris are trapped within and on the interior walls of cylinder 92. The tip unit is withdrawn from the laser unit and plunger 92 is pulled out away from the finger as shown in FIG. 3D. An indent 96 in the interior wall of cylinder 90 stops the withdrawal of plunger 92. The suction established within helps draw blood through the vaporized hole in finger 24. The blood is collected in cylinder 90. When full, cylinder 90 contains about 200 microliters. After the sample is collected, plunger 92 is pulled beyond indent 96, removed fully from cylinder 90 then discarded. Cylinder 90 containing the blood sample is untaped from finger 24 and capped for future testing.

Portable Base Unit

Figure 4:
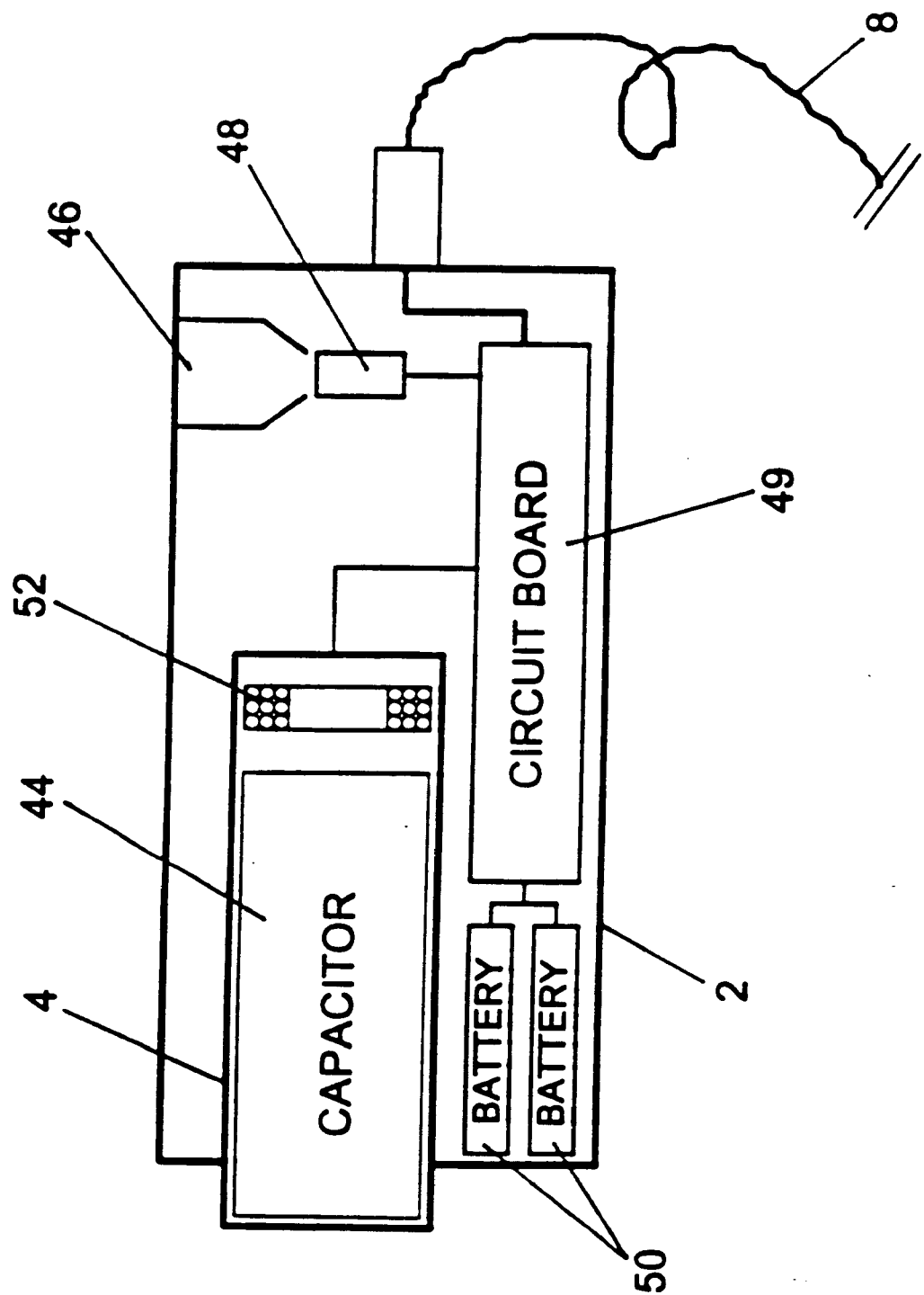
FIG. 4 shows details of the base unit of the FIG. 1 embodiment.

A drawing of the elements of portable base unit 2 in shown in FIG. 4. The unit includes system control circuitry as shown at 49, replaceable power module 4, and two 6 Volt, 0.16 Amp-hour lithium batteries 50 for system power. Base unit 2 also contains calibration aperture 46. In line with aperture 46 is laser energy detector 48 which in this embodiment is a Molectron model J9LP-1 factory-calibrated for the Erbium laser wavelength. To calibrate, the hand held unit 6 is inserted into aperture 46 and fired. The pulse energy is measured by energy detector 48 and if the pulse energy is out of calibration, the control circuitry 49 will adjust the default capacitor charging level to bring the unit back into calibration.

Power Module

Power module 4 shown in FIG. 4 includes main storage capacitor 44 which is a 40 μF and i kV capacitor as available from CSI Capacitors, Inc. The unit also contains a coil inductor 52 with inductance of 100 μH. Other power modules with different capacitance and inductance can be inserted into the base unit to modify the laser beam characteristics including pulsed duration and maximum pulse energy.

Electric Circuit

Figure 5:
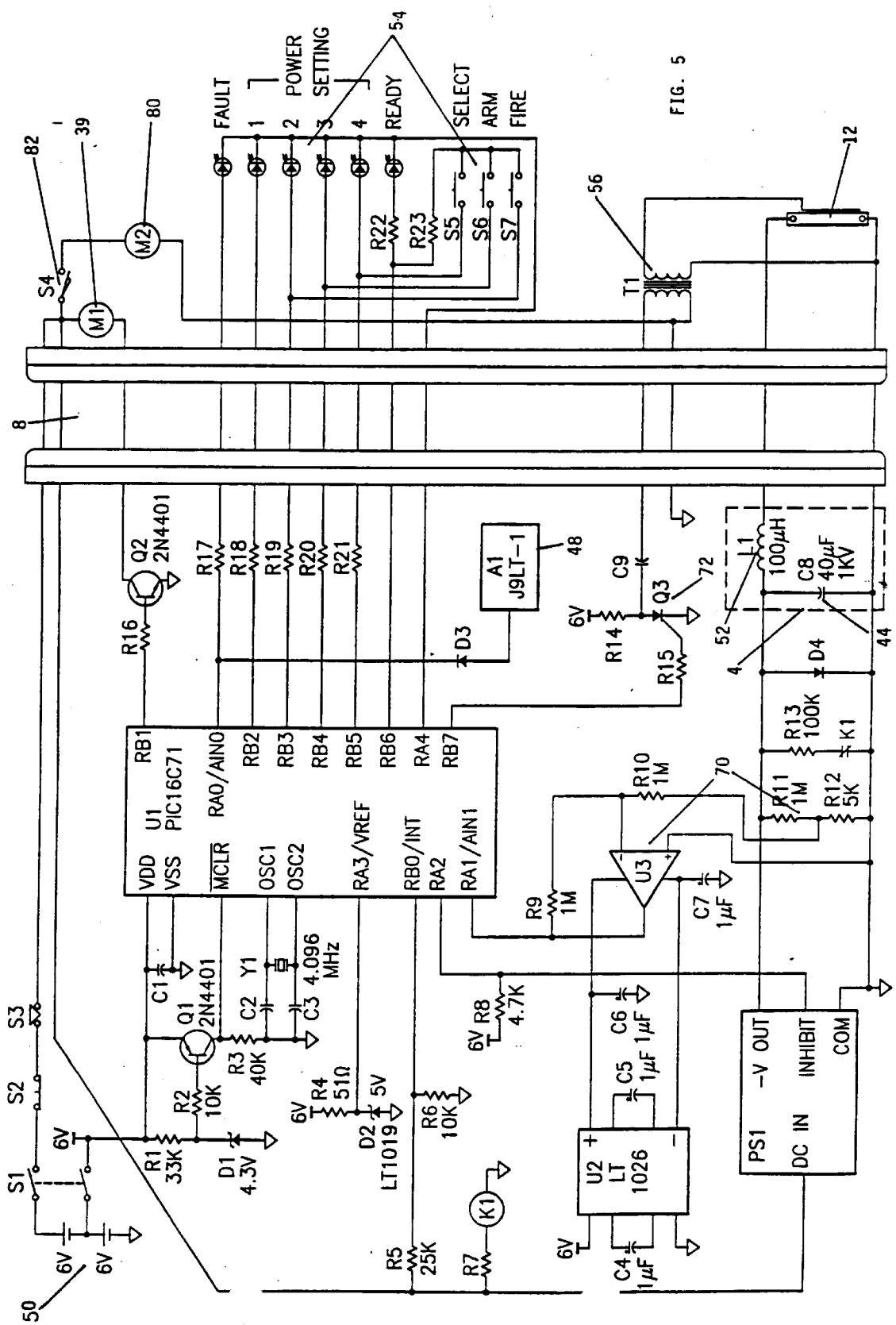
FIG. 5 is a schematic of the electric circuit for the FIG. 1 embodiment.

The electric circuit for this preferred embodiment is shown in FIG. 5. The key circuit elements in the base unit control circuitry 49 include a microprocessor U1, a 1 kV DC-DC voltage converter PS1, a voltage monitoring circuit 70, a trigger pulse generator 72, energy detector for calibration 48 and lithium batteries 50. Capacitor C8 shown at 44 and inductor L1 shown at 52 which form the key elements of power module 4. System control is provided by U1 an 8-bit CMOS RISC microprocessor and A/D converter made by MicroChip Technology, Inc. model P1C16C71. Support elements for U1 include Q1 which provides reset capability, Y1 which provides a clock, R4 and D2 which provide a voltage reference, and R5 and R6 which divide the 12 V switched line and serve as an interrupt input. Whenever an interlock is open U1 is interrupted and inhibits PS1 and lights the fault LED. U2 is a voltage converter made by Linear Technologies model LT 1026. It converts battery voltage to a positive and negative supply voltage for Op Amp U3. Precision Op Amp U3, made by Linear technologies model LT 1077, is the center of the voltage monitoring circuit 70. It inverts signals from voltage divider R11/R121 from a negative voltage to a positive one which can be fed into A/D converter on U1. When U1 senses the proper voltage on the capacitor C8, shown at 44, an inhibit signal is sent to power supply PS1. Q3 is the principle element of the trigger pulse generator. Upon a signal from U1, SCR Q3 sends a low voltage pulse to trigger transformer 56 in the hand held unit to initiate the flashlamp discharge. As the impedance of the lamp falls, energy stored in primary capacitor C8 sustains a full duration flash discharge. Q2 drives the fan motor in the hand held unit. K1 is a solid state relay that serves as an interlock relay which will discharge C8 when deenergized by an interlock opening.

The key electrical elements in the hand held unit are the laser flashlamp 12, trigger pulse transformer 56, operational switches and indicator lamps 54, fan motor 39 and laser beam safety shutter 80 which is opened only when interlock switch 82 is closed. When disposable tip 26 is firmly pressed into hand held unit 6 by finger 24, interlock switch 82 will close.

Flexible cable 8 carries control and indicator signals between hand held unit and the base unit. These signals are input into U1 through I/O pins. Cable 8 also carries the low voltage trigger to trigger transformer 56 and the primary voltage pulse from module 4 to laser flashlamp 12.

Method of Creating Preferred Hole Shape

Figure 6:
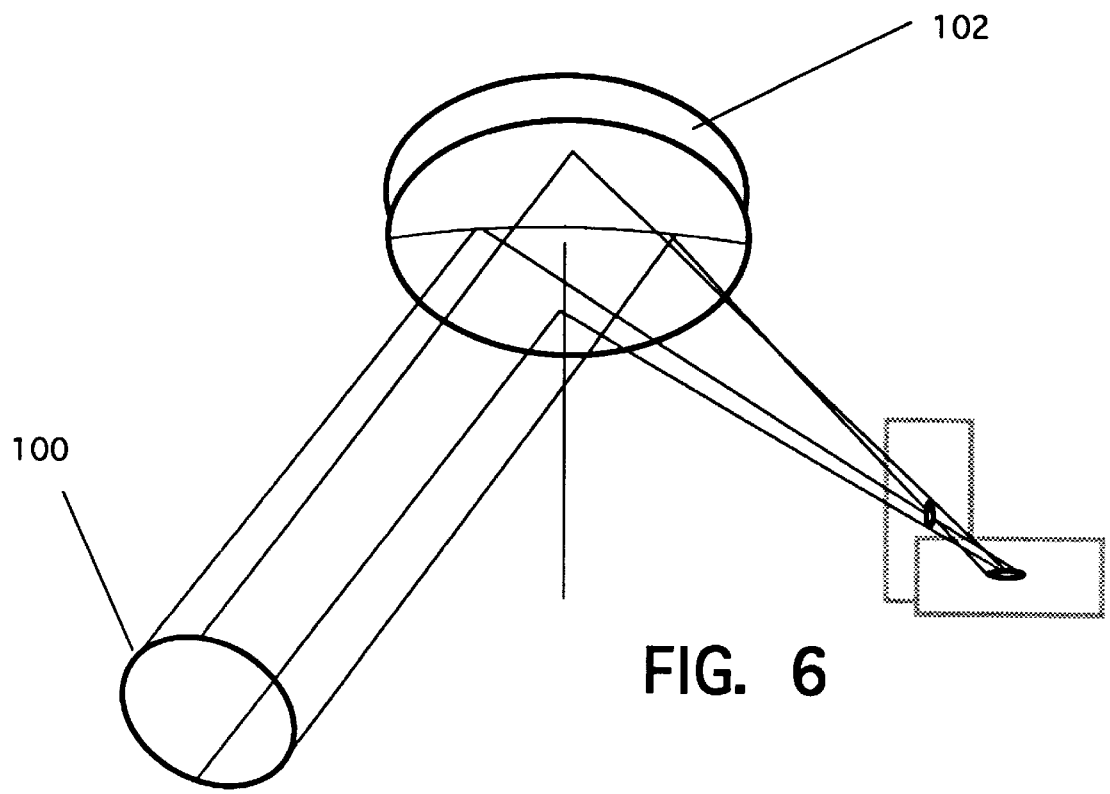
FIG. 6 shows an arrangement for producing elliptical holes.

Applicant has discovered that a an elliptical hole in the skin is better than a hole with a circular cross section. Elliptical holes seem to produce more blood with less pain than similar circular holes. A preferred arrangement for producing these elliptical holes is shown in FIG. 6. A 3 mm diameter circular beam 100 with a divergence of 3.5 milliradians is reflected off a 50 mm (radius of curvature) concave mirror 102 at an angle of incidence of 30 degrees as measured from the normal of the mirror surface. The result of this reflection is that the beam focuses twice, both times as ellipses (almost slits), one at 22 mm from the mirror and the other at 29 mm from the mirror. At the first focus, the cross section of the beam is 0.75 mm by 0.15 mm and at the second focus the cross section of the beam at focus is 1.0 mm by 0.2 mm. Excellent blood sampling holes have been obtained at both foci with single laser pulses at energies of about 300 mJ. The holes are similar to those produced by a knife blade, but the pain experienced appears to be much less for the laser than the knife blade.

Preferred Method of Trapping Vapor

Figure 7:
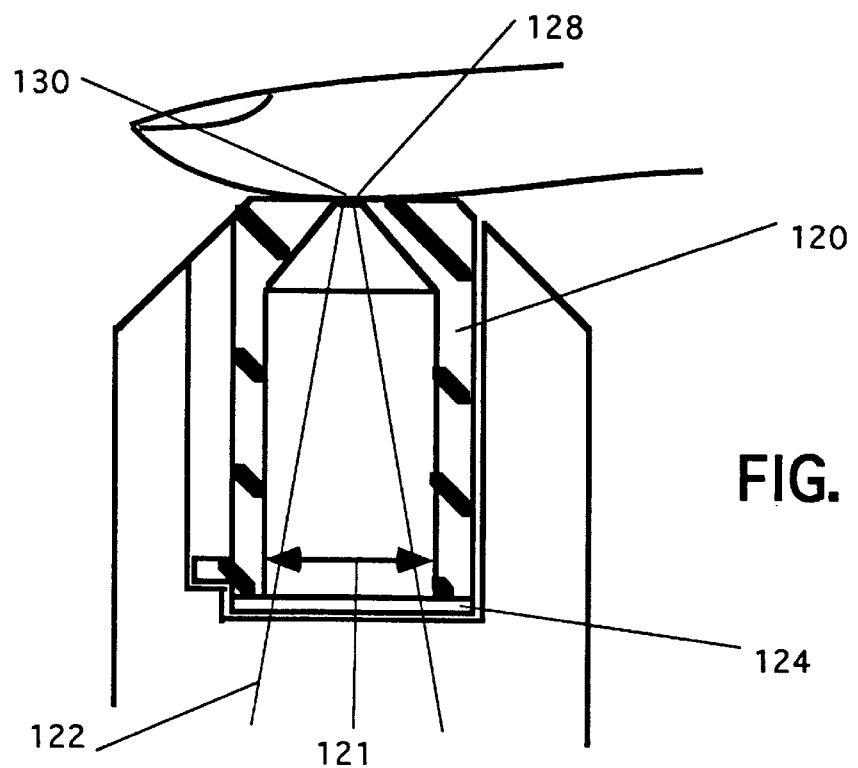
FIG. 7 shows an alternate disposable tip.

An alternate embodiment for trapping vaporized tissue is shown in FIG. 7. One end of disposable tip 120 has an inside diameter 121 larger than the diameter of incoming beam 122. This end is sealed with a plastic membrane 124 that has good transmission for the erbium laser. Good plastics for this purpose are optically clear films of polyester, polypropylene or polyethylene. The opposite end 126 has an aperture 128 that is only slightly larger than the beam spot at focus 130. Preferably the opening is shaped to coincide with the shape of the beam spot at focus and I prefer an elliptical spot as discussed in the above section. When the tip is placed firmly on the finger of the patient, the tip is sealed by the finger. The laser pulse is applied and the vaporized tissue is ejected into the tip. In a very short period of time (less than one second) substantially all of the vaporized tissue condenses to the point that there is no significant positive pressure in the tip. The tip is then removed and aperture 128 is sealed with adhesive tape to trap substantially all of the vaporized tissue. Blood from the elliptical hole in the finger is then collected on a microscope slide or on or in any other blood collector as desired in a usual manner.

While the present invention has been described in connection with a particular embodiment, it will be understood that many changes and modifications of this invention may be made by those skilled in the art without departing from the true spirit and scope of the invention. For example, as stated in the Tankovich patent laser pulses at other wavelengths can be used. The interior walls of the pump cavity can be in a diffuse-reflecting close-coupled configuration or a specular-reflecting elliptical configuration. Other feasible laser pumping techniques include arc-lamp pumping and diode laser pumping. With diode laser pumping we would need a diode driver to provide high current pulses to the pumping diodes. Crystals other than Erbium:YAG can be used. Such crystals include Erbium:YAP and Erbium:YSGG. Erbium:YSGG would be the preferred crystal if pumped by a diode laser. Many other hand grip designs such as pistol grip are possible. The system configuration can be varied. For example, the power module can be permanently attached to the hand held unit or the base unit and power module can be made a part of the hand held portion so that the entire device is hand held. Many other optical configurations will be obvious to those skilled in the art. The pulse characteristics can be varied as indicated in the Tankovich patent. Applicants have experimented with burst mode operation (several pulses in rapid succession) producing larger craters in test materials. A scanning lens, scanning mirror or other scanning devices can be used to create a lateral array of punctures like a slit from a burst of pulses. Persons skilled in the art will recognize that the pulse could be delivered by a fiber optic (which could be made disposable). Also, the pulse could be directed down a disposable blood collection capillary tube (in effect a hollow fiber optic) which could then collect the blood. The features of flow-through and sealed disposable tips shown in FIGS. 3A and 3B could be incorporated in the blood collecting tip shown in FIG. 3C. For instance, a single, side hole in the flange that supports the plastic film 28 on the plunger 92 could be added to give the blood collector tip flow-through capability for external filtering. Alternately, adding two side holes in the same flange plus a bulb and check valve could give the blood collector tip additional suction capability prior to the laser firing and additional tissue debris trapping volume after the laser firing. Also, if cylinder 90 is made of a flexible plastic and is squeezed slightly before taping to the skin, a vacuum will be created inside the cylinder when the squeeze is relaxed. The preferred pulse cross section (i.e., a cross section having a long dimension and a short dimension) can be formed in many different ways as is well known. I have had best results with a 5 to 1 ratio but a ratio as low as 3 to 1 would be better than circular. I recommend a ratio of somewhere between 3 to 1 and 15 to 1. The preferred pulse energy density is 2 to 3 Joules/mm$^2$. I recommend energy densities of between 1 to 4 Joules/mm$^2$. Other methods of obtaining elongated sample holes in the skin is to use two cylindrical lens surfaces at right angles or one cylindrical lens surface and one spherical lens surface.

Accordingly, the appended claims are intended to cover all such changes and modifications as fully within the true spirit and scope of the present invention.

I claim:

1. A laser device for obtaining blood samples through skin of humans or animals, said device comprising:

A) a laser crystal,

B) optical resonator comprising at least two mirror surfaces optically located on opposite sides of said laser crystal, C) a laser pumping means to produce from said crystal and resonator at least one short duration laser pulse defining a beam path and having sufficient energy when shaped and focused to vaporize skin tissue, D) a power supply means for providing power to said laser pumping means, E) a pulse shaping means for shaping and focusing said laser pulse to produce at at least one location along said beam path, defining a sampling location, a pulse cross section having a long dimension and a short dimension, said long dimension being at least three times longer than said short dimension, and F) a vapor trap means for trapping tissue vapor produced at said sample location said vapor trap means comprising a filter means for filtering said tissue vapor and a fan means contained in said housing for providing cooling air for said laser crystal and a suction source for sucking air and vaporized tissue into said filter means.

2. A laser device as in claim 1 wherein said crystal is an Erbium:YAG crystal.

3. A laser device as in claim 1 wherein said crystal is an Erbium:YSGG crystal and said pumping means comprises a laser diode.

4. A laser device as in claim 1 wherein said power means is contained in a base unit and said laser crystal and laser pumping means is contained in a hand held housing, said base unit being connected to said hand held housing with a flexible electric power cable.

5. A laser device as in claim 1 wherein said vapor trap means comprises a seal means for sealing said vaporized tissue inside a disposable container.

6. A laser device as in claim 1 and further comprising a disposal tip means for collecting tissue vapor, said tip means comprising an aperture, located at said sampling location, with a cross section only slightly larger that the cross section of said laser pulse at said sampling location.

7. A laser device as in claim 1 and further comprising a disposal tip means for collecting tissue vapor, said tip means comprising an aperture, located at said sampling location, with a cross section shaped to match the cross section of said laser pulse at said sampling location and said cross section of said aperture being only slightly larger that the cross section of said laser pulse at said sampling location.

8. A laser device as in claim 1 and further comprising a beam energy detector and a calibration circuit means for keeping the device calibrated based on calibration pulses directed at the detector.

9. A laser device as in claim 1 wherein said long dimension is approximately five times longer than said short dimension.

10. A laser device as in claim 1 wherein said pulse shaping means comprises a concave mirror to shape the cross section of said at least one pulse into two elliptical cross sections at two spaced apart focal planes.

11. A laser device as in claim 1 wherein said sufficient energy is between 200 mJ and 400 mJ.

12. A laser device as in claim 11 wherein said pulse defines an average energy density at said sample location and said energy density is between 1 J/mm$^2$ and 4 J/mm$^2$.

13. A laser device as in claim 1 wherein said pumping means comprises a flash lamp and said power supply means comprises a capacitor for supplying high voltage power to said flash lamp.

14. A laser device as in claim 13 wherein said base unit comprises a port for said power module, said power module being removable from said port and connected directly to said laser unit to permit said high voltage pulse to be provided from said capacitor to said flash lamp.

* * * * *